US012697501B2

(12) United States Patent
Law et al.

(10) Patent No.: US 12,697,501 B2
(45) Date of Patent: *Aug. 4, 2026

(54) SYSTEM AND METHOD OF GENERATING HIGH VOLTAGE VARIABLE FREQUENCY ELECTROMAGNETIC RADIATION

(71) Applicant: Advanced Biotechnologies, LLC, Brewster, MA (US)

(72) Inventors: James William Law, Brewster, MA (US); James David Girard, Brewster, MA (US); Colin Bester, Dripping Springs, TX (US)

(73) Assignee: Advanced Biotechnologies, LLC, Brewster, MA (US)

( * ) Notice: Subject to any disclaimer, the term of this patent is extended or adjusted under 35 U.S.C. 154(b) by 863 days.

This patent is subject to a terminal disclaimer.

(21) Appl. No.: 17/882,089

(22) Filed: Aug. 5, 2022

(65) Prior Publication Data

US 2023/0097778 A1 Mar. 30, 2023

Related U.S. Application Data

(60) Continuation of application No. 16/281,550, filed on Feb. 21, 2019, now Pat. No. 11,420,070, which is a
(Continued)

(51) Int. Cl.
*A61N 1/40* (2006.01)
*A61N 1/02* (2006.01)
*H01J 37/24* (2006.01)

(52) U.S. Cl.
CPC .............. *A61N 1/40* (2013.01); *A61N 1/025* (2013.01); *A61N 1/403* (2013.01); *H01J 37/241* (2013.01)

(58) Field of Classification Search
CPC . A61N 1/025; A61N 1/08; A61N 1/40; A61N 1/403
See application file for complete search history.

(56) References Cited

U.S. PATENT DOCUMENTS

| | | | |
|---|---|---|---|
| 3,600,604 A | 8/1971 | Thorne-Booth | |
| 3,842,312 A | 10/1974 | Emmons | |
| (Continued) | | | |

FOREIGN PATENT DOCUMENTS

| | | | |
|---|---|---|---|
| AU | 692858 B2 | 6/1998 | |
| CA | 2638667 A1 | 2/2010 | |
| (Continued) | | | |

OTHER PUBLICATIONS

European Search Report for European Application No. EP1819381, mailed on Jun. 6, 2019 (7 pages).
(Continued)

*Primary Examiner* — Tigist S Demie
(74) *Attorney, Agent, or Firm* — Goodwin Procter LLP

(57) ABSTRACT

In a high voltage, variable frequency radiation generation system, a carrier signal supplied to a primary coil of a transformer is varied, e.g., turned ON and OFF at variable frequencies. The ON duration and/or the average amplitude of the carrier signal may also be varied. Moreover, the carrier signal may be modulated using an audio signal. The parameters to control the variation of the carrier can be provided as a recipe via a software application. A server can provide different types of apps providing different control features. The server may also collect user characteristic data and recipe usage data, and may facilitate exchange of these data and may recommend recipes based on a particular user characteristic.

6 Claims, 2 Drawing Sheets

Related U.S. Application Data division of application No. 14/729,627, filed on Jun. 3, 2015, now Pat. No. 10,252,072.

(60) Provisional application No. 62/007,145, filed on Jun. 3, 2014.

(56) References Cited

U.S. PATENT DOCUMENTS

| | | | |
|---|---|---|---|
| 4,114,685 A | 9/1978 | Schwartz et al. | |
| 4,410,837 A | 10/1983 | Suzuki et al. | |
| 4,500,879 A | 2/1985 | Smith, III et al. | |
| 5,144,207 A | 9/1992 | Brunson | |
| 5,286,495 A | 2/1994 | Batich et al. | |
| 5,350,414 A * | 9/1994 | Kolen | A61N 1/025 |
| | | | 607/46 |
| 5,908,444 A | 6/1999 | Azure | |
| 6,149,679 A | 11/2000 | Di Mino et al. | |
| 6,211,799 B1 | 4/2001 | Post et al. | |
| 7,400,487 B1 | 7/2008 | Bitar | |
| 7,412,340 B2 | 8/2008 | Butters | |
| 7,451,839 B2 | 11/2008 | Perlman | |
| 7,583,172 B2 | 9/2009 | Koonce | |
| 7,675,731 B2 | 3/2010 | Bitar | |
| 7,817,401 B2 | 10/2010 | Messer | |
| 7,958,809 B1 | 6/2011 | Bitar et al. | |
| 7,960,867 B2 | 6/2011 | Issa et al. | |
| 8,004,816 B1 | 8/2011 | Adler | |
| 8,098,472 B2 | 1/2012 | Messer | |
| 2002/0175068 A1 | 11/2002 | Hammerstrom et al. | |
| 2005/0087989 A1 | 4/2005 | Holcomb | |
| 2007/0103686 A1 | 5/2007 | Tornkvist et al. | |
| 2010/0222850 A1 | 9/2010 | Kivlighan | |
| 2011/0156494 A1 | 6/2011 | Mashinsky | |
| 2012/0004694 A1 * | 1/2012 | Ludwig | A61N 1/3706 |
| | | | 607/7 |
| 2012/0249145 A1 | 10/2012 | Lai et al. | |
| 2013/0200855 A1 | 8/2013 | Christensen et al. | |

FOREIGN PATENT DOCUMENTS

| | | | |
|---|---|---|---|
| CN | 1125537 | A | 7/1996 |
| CN | 2421778 | Y | 2/2001 |
| CN | 202206193 | U | 4/2012 |
| CN | 202929928 | U | 5/2013 |
| CN | 103501561 | A | 1/2014 |
| EP | 0086033 | A2 | 8/1983 |
| EP | 0702316 | A1 | 3/1996 |
| EP | 0965350 | A1 | 12/1999 |
| EP | 1022933 | A2 | 7/2000 |
| EP | 1691426 | A2 | 8/2006 |
| JP | S619440 | A | 1/1986 |
| JP | 2004103520 | A | 4/2004 |
| JP | 2010051683 | A | 3/2010 |
| WO | WO-1998057704 | A1 | 12/1998 |
| WO | WO-03075964 | A1 | 9/2003 |
| WO | WO-2008156814 | A1 | 12/2008 |
| WO | WO-2009042214 | A1 | 4/2009 |
| WO | WO-2013102241 | A1 | 7/2013 |
| WO | WO-2014039647 | A1 | 3/2014 |

OTHER PUBLICATIONS

International Search Report and Written Opinion for International Patent Application No. PCT/US2015/033965 mailed Dec. 2, 2015 (15 pages).

Canadian Examination Report issued in CA No. 2988075 mailed, Jan. 20, 2022. (4 pages).

* cited by examiner

SYSTEM AND METHOD OF GENERATING HIGH VOLTAGE VARIABLE FREQUENCY ELECTROMAGNETIC RADIATION

CROSS-REFERENCE TO RELATED APPLICATIONS

This application is a Continuation of U.S. patent application Ser. No. 16/281,550, filed on Feb. 21, 2019 which is a Divisional of U.S. patent application Ser. No. 14/729,627, filed on Jun. 3, 2015, which claims priority to and benefit of U.S. Provisional Patent Application Ser. No. 62/007,145 filed on Jun. 3, 2014, the entire content of each of which is hereby incorporated by reference in its entirety.

FIELD OF THE INVENTION

The present invention generally relates to generation of electromagnetic radiation and, in particular, to controlled generation of multi-frequency, high voltage electromagnetic radiation and spectral emissions.

BACKGROUND

Some recent studies indicate that a subtle energy field may exist around living organisms. This electrical field may include frequencies that the body of an organism may produce or absorb, e.g., to facilitate improved health and wellness. According to these studies, the subtle energy may regulate optimum cell function and lack of or imbalance of such energy may be the cause of illness or sub-optimal biological function.

According to various studies, the body of a living being has the inherent ability to selectively absorb the needed frequencies through cells of the skin, nerves, muscles, connective tissues, and organs. As such, controlled electromagnetic pulses may provide a jump-start to dysfunctional cell-level electrical systems, e.g., those experiencing significant impedance to proper signal flow and thereby adversely affecting function of such systems. Exposing the body to controlled electromagnetic radiation, therefore, can help in improving wellness.

Some devices such as Rife machines, multi-wave oscillators, various photonic light therapeutic devices, and BioCharger™ can generate and deliver electromagnetic energy to a subject. The electromagnetic radiation generated by these devices cannot be readily controlled, however, to customize the delivery of energy to the subject. For example, one or more properties of the generated electromagnetic radiation, such as power level, pulse frequencies, etc., cannot be controlled in response to user feedback or based on data collected from a number of users. Resonant transformers (e.g., open-core or air-core transformers) that are commonly known as Tesla coils have been used for a number of years to generate high voltage signals and plasma discharge. In general, the output of these Tesla coils is not finely tuned and/or controlled, however. Improved systems and methods allowing accurate control of electromagnetic radiation to be delivered to a subject are therefore needed.

SUMMARY

In various embodiments, the present invention features custom-controlled delivery of pulsed electromagnetic field that can bathe the whole body in a rich field of bio-compatible frequencies and light. This is achieved, at least in part, by controlling the switching of a carrier signal in a solid-state open core transformer. Specifically, the switching frequency and/or duty cycle of the switching can be varied. Alternatively, or in addition, the root-mean-squared (RMS) voltage of the carrier signal is varied according to a control signal and/or the carrier signal is modulated using an audio signals. Several recipes may be presented to users for convenient control of the electromagnetic radiation, where each recipe can be a unique combination of one or more parameters described above. Based on a user characteristic (e.g., blood pressure, pulse rate, etc.) a suitable recipe may be recommended to the user.

Accordingly, in one aspect, a system for generating electromagnetic radiation include a resonant transformer having a primary coil and a secondary coil and a pulse generator generating a carrier signal using an input DC voltage signal. The system also includes a switch that is connected to the pulse generator, and that is switched at a varying switching frequency, so as to supply a variably switched carrier signal to the primary coil. The switch is controlled such that the switching frequency of the carrier signal is varied from a start frequency to an end frequency during a specified period. The frequency variation can be a linear variation, an exponential variation, a saw tooth variation, or a combination of any two or all three of the three types of variations. The switch may be alternately turned ON and OFF at the varying switching frequency such that the variably switched carrier signal includes a sequence of on-off-keyed (OOK) pulses.

In some embodiments, the specified period during with the carrier frequency is varied includes a first sub-period and a different, second sub-period. The switching frequency may be varied during the first sub-period according to a first variation (e.g., linear, exponential, or saw-tooth), and during the second sub-period according to a different second variation. In particular, each of the first and second variations can be a linear variation, an exponential variation, a saw tooth variation, or a variation based on several preset frequencies. The variations in the two sub-periods, however, are different. The several preset frequencies used for the variation may be specified by a user. Each of the start frequency and the end frequency may be selected from frequencies in a range from 1 Hz up to 100 kHz. In some embodiments, the start frequency is less than the end frequency, and the end frequency is up to one half of a frequency of the carrier signal. Alternatively, the start frequency can be greater than the end frequency, and the start frequency can be up to one half of a frequency of the carrier signal. In some embodiments, switching of the switch produces a sequence of pulses of the carrier signal, and the switch is controlled such that width of the pulses is selected according to a pulse width control signal.

In some embodiments, the system further includes a variable direct current (DC) power supply generating a variable DC voltage signal. The pulse generator is connected to the variable DC power supply, and the input DC voltage signal, which is used to generate the carrier signal, includes the variable DC voltage signal. The variable DC power supply may be controlled according to a gain signal so as to adjust voltage of the variable DC voltage signal, so as to adjust root-mean-squared (RMS) voltage of the carrier signal according to the gain signal. The gain signal may include a pulse width modulated (PWM) control signal. In some embodiments, the variable DC power supply is controlled according to an audio signal so as to vary voltage of the variable DC voltage signal. As such, the carrier signal is modulated according to the audio signal. The audio signal may include: (i) a stored audio signal, (ii) an external audio signal received at an audio port, or (ii) a mixed audio signal including the stored audio signal and the external audio signal. In various embodiments, the system may further include a number of gas-filled tubes, where each tube is disposed to receive electromagnetic radiation from the secondary coil. Each tube may include a different gas that, if excited by a voltage signal at a particular frequency, can emit a radiation.

In another aspect, a system for generating electromagnetic radiation includes a resonant transformer having a primary coil and a secondary coil. The system also includes a variable, direct current (DC) power supply generating a DC voltage signal. The DC voltage signal is generated according to both: (i) an input gain signal, and (ii) an input audio signal. An average voltage of the DC voltage signal is controlled by the gain signal and the DC voltage signal is further modulated by the audio signal. The system also includes a pulse generator connected to the variable DC power supply, generating a modulated carrier signal using the modulated DC voltage signal. Thus, the carrier signal can be adjusted according to the input gain signal and also the input audio signal.

The gain signal may include a pulse width modulated (PWM) control signal, and the audio signal may include one of: (i) a stored audio signal, (ii) an external audio signal received at an audio port, and (ii) a mixed audio signal comprising the stored audio signal and the external audio signal. The external audio signal may be received at the audio port via a network such as the Internet, a user's private home network, etc. In various embodiments, the system further includes a number of gas-filled tubes, where each tube is disposed to receive electromagnetic radiation from the secondary coil, and includes a different gas that, if excited by a voltage signal at a particular frequency, emits a different radiation. The electromagnetic radiation received by the gas tubes from the secondary coil can generate such voltage signal. The radiation emitted by the gas tubes may be used for therapeutic purposes.

In another aspect, a controller for controlling an electromagnetic radiation generation system includes a processor and a memory coupled to or in communication with the processor. The memory includes instructions which, when executed by the processor, program the processor to transmit a recipe to the electromagnetic radiation generation system. The recipe includes a mode, a start frequency and an end frequency, and a duration. The mode may include one or more of: (i) a linear variation, (ii) an exponential variation, and (iii) a saw tooth variation. Thus, the frequency at which a carrier signal supplied to the electromagnetic radiation generation system is switched can be varied according to a selected mode. The recipe may also include an output scale factor, a pulse width factor, or both. The output scale factor can be used to adjust gain of a carrier signal supplied to the electromagnetic radiation generation system. The carrier may be supplied in the form of bursts, and the duration of the bursts can be selected using the pulse width factor.

In some embodiments, the instructions further program the processor to identify at least one recipe according to a user profile. To this end, the instructions may further program the processor to receive a characteristic corresponding to a user profile, and to store the characteristic in a profile database. The memory may include a recipe database having a number of recipes. The instructions may program the processor to select, in response to a user input, one or more recipes from the recipe database. The selected recipes may control the electromagnetic radiation generation system such that the radiation generated thereby can have a therapeutic effect on a user. The recipe, however, may be customized for a user according to a characteristic such as pulse rate, blood pressure, age, etc.

In some embodiments, the instructions further program the processor to receive an update to the recipe database, e.g., to modify a previously stored recipe and/or to receive one or more new recipes. Alternatively or in addition, the instructions can program the processor to receive, via a network, updated instructions in the memory. The controller may include a wireless transceiver for wirelessly transmitting the recipe to the electromagnetic radiation generation system. In some embodiments, the controller includes a voltage sensor sensing an output voltage of the electromagnetic radiation generation system, and/or a current sensor sensing an output current of the electromagnetic radiation generation system. The controller may be adapted to turn off the electromagnetic radiation generation system if the sensed output voltage exceeds a specified maximum voltage threshold, and/or the sensed output current exceeds a specified maximum current threshold. The controller may include or may be implemented using a smartphone, a tablet computer, a laptop, or a desktop computer.

In some embodiments, the instructions further program the processor to synthesize a new recipe in response to a user input corresponding to one or more parameters of the recipe. In addition, the instructions may program the processor to: (i) store the new recipe in the memory, (ii) transmit the new recipe to a server, for storage and/or analysis thereby, and/or (iii) to transmit the new recipe to the electromagnetic radiation generation system. The instructions stored and executed by the controller can also program the processor to (i) start, (ii) stop, (iii) suspend, and/or (ii) resume operation of the electromagnetic radiation generation system according to a transmitted recipe.

In another aspect, a method for generating electromagnetic radiation includes selecting a root-mean-squared (RMS) voltage of a carrier signal using a gain control signal, and modulating the carrier signal using an audio signal. The method also includes supplying the modulated carrier signal to a primary coil of an resonant transformer, for generation of electromagnetic radiation by the resonant transformer. The RMS voltage of the carrier signal may be selected from about 50 V up to about 300 V. The method may also include receiving electromagnetic radiation produced by an output signal from a secondary coil of the resonant transformer at each one of a number of gas-filled tubes. Each tube may be filled with a different gas that, if excited by the output signal at a particular frequency, can emit radiation.

In some embodiments, the method includes varying the carrier signal using a sequence of pulses. The frequency of the pulses may be substantially constant, or may be varied from a first frequency to a second frequency during a specified period. The variation can be: (i) a linear variation, (ii) an exponential variation, and (ii) a variation based on a number of preset frequencies, or a combination of any two or all three of these. Alternatively or in addition, the method may include adjusting or changing a width of the pulses used to vary the carrier signal.

In another aspect, a method for delivering electromagnetic radiation to a subject includes receiving a selection of a recipe having one or more of a modulation style, a reference to an audio file, a mode, a start frequency, an end frequency, a duration of treatment, a pulse width, and an output scale factor. The method also includes varying a carrier signal according to the selected recipe, and supplying the varied carrier signal to a primary coil of an resonant transformer. In addition, the method includes receiving electromagnetic radiation produced by an output signal from a secondary coil of the resonant transformer at each one of a number of gas-filled tubes. Each tube may be filled with a different gas that, if excited by the output signal at a particular frequency, emits a radiation.

The modulation style may include audio modulation and/or frequency sweeping. In some embodiments, the modulation style includes audio modulation, and the recipe includes a reference to a song that can be used to provide an audio signal for modulation of the carrier. In some embodiments, the mode includes a linear variation and/or a logarithmic variation of a frequency of switching of the carrier. The start frequency or the end frequency, or both may be selected from frequencies in a range from 5 Hz up to 50 kHz. The start frequency can be less than or greater than the end frequency. In some embodiments, the method includes receiving a characteristic of a subject, and presenting for selection one or more recipes based on, at least in part, the received characteristic. Alternatively or in addition, the method may include receiving a characteristic of a subject, and presenting for selection one or more modified recipe parameters of a selected recipe, the modification being based on, at least in part, the received characteristic. The characteristics may include one or more of user's temperature, pulse rate, respiration rate, blood pressure, electroencephalogram (EEG), etc. A recipe can thus be customized according to one or more user characteristics, and that customized recipe can be used to control the radiation to be delivered to the user, for beneficial effect on the user.

In another aspect, a computer-implemented method of analyzing recipes includes receiving at a server, usage data corresponding to each one of several users exposed to electromagnetic radiation generated by one or more resonant electromagnetic radiation devices. The usage data corresponding to each user may include one or more user characteristics. The usage data may also include one or more recipes and an indication of usage of each of the one or more recipes. The recipes may be used to control a resonant electromagnetic radiation device while the user was exposed to radiation from the device, and each recipe may include a respective modulation style.

The method also includes correlating by the server: (i) each user characteristic from the usage data for the various users, (ii) each recipe from the usage data for the various users, and (iii) the indicia of usage of that recipe, to compute a correlation between a user characteristic and a recipe. In addition, the method includes generating a recipe database having one or more user characteristics and a corresponding set of recipes based on, at least in part, the correlation, computed using the usage data, between the user characteristic and each of the recipes. In this way, one or more recipes that are effective for users having particular characteristic(s), or are perceived to be effective by users having the particular characteristic(s), can be identified. Those recipes can then be recommended to users having the particular characteristic(s).

The usage data corresponding to one or more users may receive from a social medium account (e.g., Facebook™, Twitter™, or WhatsApp™ account) of the user. Alternatively or in addition, the usage data corresponding to one or more users may be received from a resonant electromagnetic radiation device, where the user has been exposed to radiation from that device. The usage data corresponding to one or more users may be received via a network, e.g., the Internet. One or more user characteristics of one or more users may include user's temperature, pulse rate, respiration rate, blood pressure, and/or electroencephalogram (EEG).

The indication of usage may include a frequency of usage and/or an effectiveness measure.

In some embodiments, the method includes receiving a user characteristic at the server, separately from any usage data. Such a characteristic may be received from a user who has not previously used the resonant electromagnetic radiation device and, as such, may benefit from guidance in selecting a suitable recipe for controlling the device. In these embodiments, the method also includes selecting a user characteristic from the recipe database that matches with the user characteristic received separately, and transmitting to a destination at least one recipe from the set of recipes corresponding to or correlating with the selected user characteristic. The destination can be a social medium account of a user and/or a controller of a resonant electromagnetic radiation device.

In another aspect, a computer-implemented method of exchanging recipes includes receiving at a server, at least one usage data element corresponding to each one of several users exposed to electromagnetic radiation generated by one or more resonant electromagnetic radiation devices. Each usage data element may include one or more user characteristics; one or more recipes used to control a resonant electromagnetic radiation device while the user was exposed to radiation from the device, and an indication of usage of each of the one or more recipes. Each recipe may include a modulation style.

The method also includes storing, by the server, the usage data in a usage database and receiving a specified user characteristic at the server. In addition, the method includes selecting by the server one or more usage data elements from the usage database such that at least one user characteristic in each of the selected usage data elements matches with the specified user characteristic, and displaying one or more recipes corresponding to the selected one or more usage data elements. In this way, if a user provided the specified user characteristic to the server, the server may present to that user the recipes used by other users having a similar characteristic.

One or more usage data elements corresponding to a user may be received, via a network, from a social medium account of the user and/or a controller of an resonant electromagnetic radiation device used by the user. The modulation style may include audio modulation, and the recipe may further include an audio file identifier, such as a reference to a memory location in storage, a link to a song file on the Internet, a home network, etc. In some embodiments, the modulation style includes frequency sweep, and the recipe further includes: (i) a first frequency, (ii) a second frequency, and (iii) a sweep duration. According to the recipe, a switching frequency of the carrier may be swept from the first frequency to the second frequency during the sweep duration.

The indication of usage corresponding to a recipe may include a frequency of usage of the recipe, and/or a user specified effectiveness of the recipe. The method may include sorting by the server the one or more displayed recipes according to indicia of usage thereof. In some embodiments, the method may include transmitting one or more displayed recipe to a controller of a resonant electromagnetic radiation device that may be used by a user who provided the specified characteristic.

In some embodiments, the method includes generating a customized recipe by combining a first parameter from a first selected/displayed recipe and a second parameter from a second selected/displayed recipe, and transmitting the customized recipe to a controller of an resonant electromagnetic radiation device that may be used by a user who provided the specified characteristic. Each of the first and second parameters may include any of: (i) a first frequency, (ii) a second frequency, and (iii) a sweep duration.

In another aspect, a computer system is configured to transmit a web-enabled user interface to a web-enabled user device. The user interface enables the computer system to: (a) control an open core electromagnetic radiation device via the user device, and/or (b) receive a state of the electromagnetic device via the user device. The user interface includes one or more of: (i) a command to operate the electromagnetic radiation device, or (ii) a command to access a state of the electromagnetic radiation device, or (iii) an operation parameter of the electromagnetic radiation device. The user interface may include a RESTful application program interface (API). The user device can be a smartphone, a tablet computer, a laptop, or a desktop computer.

The command to operate the electromagnetic radiation device may include one or more of: (i) a start command, (ii) a stop command, (iii) a pause command, and (iv) a resume command. The command to operate the electromagnetic radiation device may include a command to set an operation parameter of the electromagnetic device according to a specified value. The state of the electromagnetic radiation device may include a running state or an off state. The command to access the state of the electromagnetic radiation device may include a command to receive a value of an operation parameter of the electromagnetic device. The operation parameters may include one or more of: (i) a modulation style, (ii) a start frequency, (iii) an end frequency, (iv) a duration, (v) an output scale factor, and (vi) a pulse width. The computer system may be further configured to update a web-enabled user interface transmitted previously to a web-enabled user device.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals generally refer to the same or similar elements. In different drawings, the same or similar elements may be referenced using different reference numerals. The drawings are not necessarily to scale, emphasis instead being placed upon illustrating aspects of the invention. In the drawings.

DETAILED DESCRIPTION

Figure 1:
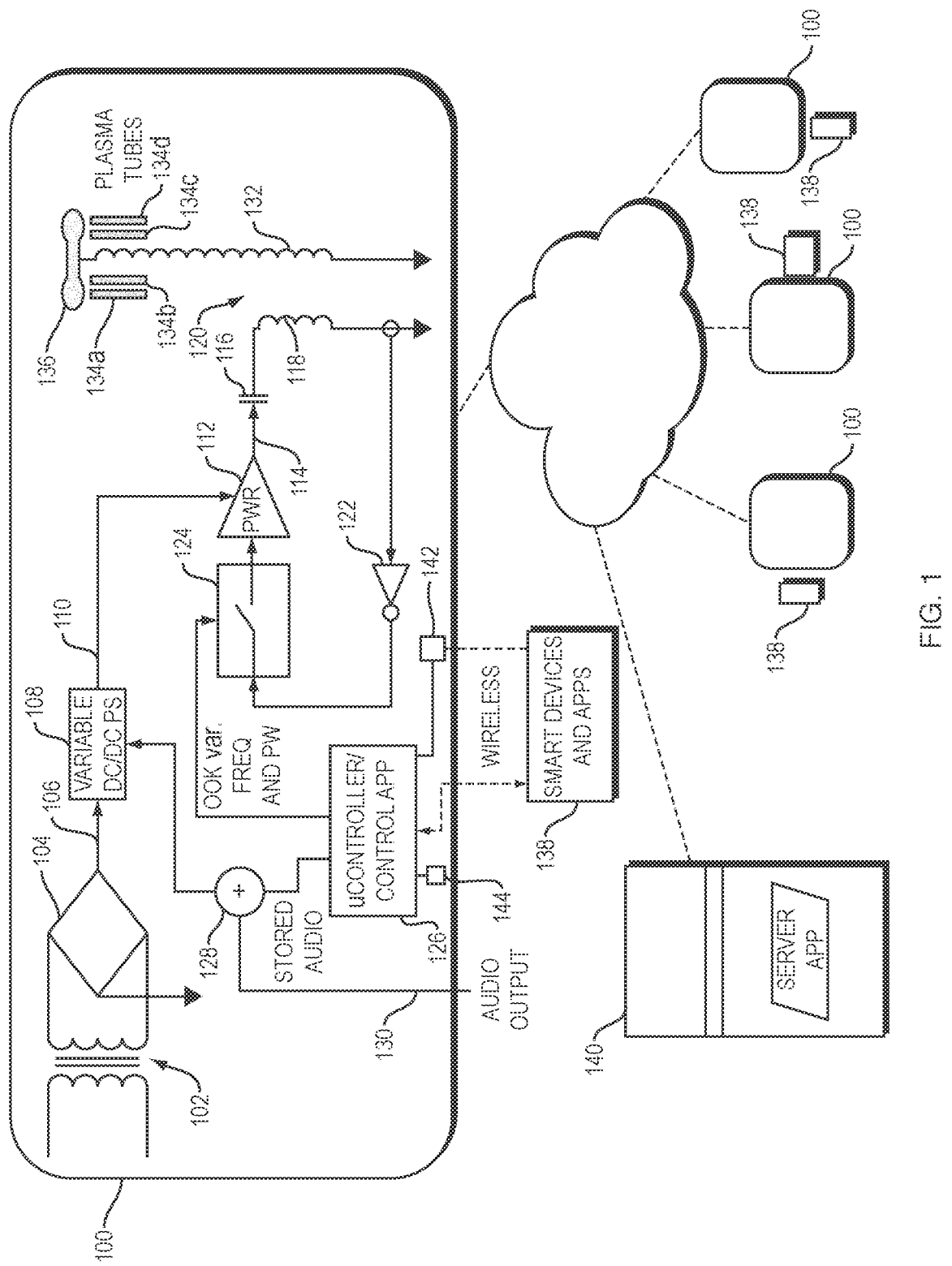
FIG. 1 schematically depicts an example of a high voltage, variable frequency electromagnetic radiation system and associated computing devices, according to one embodiment.

In one embodiment, a high voltage multi-frequency system 100 that is schematically depicted in FIG. 1, supply from A/C mains (110V or 230V) is supplied via a transformer 102 to a rectifier 104, so as to obtain a DC output 106. The DC output 106 is supplied to an adjustable DC-DC power supply 108, and the output 110 thereof is received by the pulse generator 112. The pulse generator 112 produces at the output port 114 thereof a carrier signal, i.e., a sequence of pulses, that is supplied via a capacitor 116 to the primary coil 118 of the resonant transformer 120. A sensor 122 can sense current passing through the primary coil 118 and provide a feedback to the pulse generator 112 via a controllable switch 124. If the switch 124 is maintained closed, feedback from the sensor 122 can be used to tune the frequency of the carrier generated by the pulse generator 112 such that the carrier frequency is approximately the same as (i.e., within ±5%) the resonant frequency of the primary circuitry of the resonant transformer 120. The resonant frequency is determined by the inductance L of the primary coil 118 and the capacitance C of the capacitor 116. In one embodiment, the resonant frequency and the carrier frequency is about 200 kHz. Either one or both of the capacitor 116 and the primary coil 118 can be selected suitably to change the resonance frequency, e.g., to 150 kHz, 250 kHz, 300 kHz, etc.

A processor 126 can control the DC output voltage at the output 110 of the power supply 108 which, in turn, can adjust the root-mean-squared (RMS) voltage of the carrier signal. To this end, the processor 126 can control a gain parameter. For example, the processor 126 may supply a digital value to a digital-to-analog converter and the voltage level of the analog signal, as specified by the digital value, can be used to adjust the output voltage of the power supply 108. In some embodiments, the processor can output a pulse-width modulated (PWM) signal, and the encoding of the PWM signal can be used to adjust the output voltage of the power supply 108. In one embodiment, the output voltage of the power supply 108 can be adjusted to any value within the range of 50-300V DC.

Additionally or in the alternative, the processor 126 can provide a stored audio signal (e.g., a song), via a selector/mixer 128, to control the output DC voltage supplied by the variable DC-DC power supply 108 at the output 110. Specifically, the output voltage can be varied according to instantaneous frequencies of the stored audio signal. As the output voltage is used to generate the carrier frequency, the amplitude of the carrier can also vary according to the instantaneous frequencies of the audio signal, thereby resulting amplitude modulation of the carrier. In some embodiments, alternatively or in addition, an audio signal can be received from an external source (e.g., a smart phone, CD player, etc.) at an audio input port 130, and can be used to modulate the carrier in a manner similar to amplitude modulation using the stored audio signal. The audio signal may be received or streamed via a network (such as the Internet, a user's home network, etc.), as well. In some embodiments, the audio signal received at the port 130 and the stored audio signal supplied by the processor 126 can be combined in the selector/mixer 128, and the combined signal can be used to modulate the carrier. It should be understood that some embodiments do not provide for amplitude modulation of the carrier.

The switch 124 can be controlled by software executed on the processor 126. Specifically, the processor 126 can control the switching frequency, i.e., the frequency at which the switch 124 can be turned ON and OFF. The switching frequency can be as low as 1 Hz and as high as 100 kHz. In general, in some embodiments, the switching frequency can be up to one half of the carrier frequency. For example, if the carrier frequency is 400 kHz, the switching frequency can be as high as 200 kHz. The on-off-keying (OOK) of the carrier that is caused by the switching operation can result in producing harmonics of the carrier. Additionally, or in the alternative, the processor 126 can control a pulse width corresponding to the switching, i.e., the ON duration of the switch within a period corresponding to a particular switching frequency. The ON duration for any interval can be varied from 0 to 100%, 0% indicating that the switch is entirely OFF for a particular interval and 100% indicating that the switch is always ON during a particular interval. Typical examples of the pulse width, i.e., the ON duration include 10%, 20%, 25%, 40%, 50%, 60%, 70%, 75%, 80%, 90%, etc. By controlling the pulse width, the total amount of energy delivered to the primary coil 118 during a specified duration can be controlled.

In various embodiments, the processor 126 varies the switching frequency from an initial value to a final value over a specified duration. The initial value can be any value in a range from 1 Hz up to 100 kHz. For example, the initial value can be 1 Hz, 10 Hz, 200 Hz, 1 kHz, 1.5 kHz, 20 kHz, 50 kHz, 100 kHz, etc. Similarly, the final value can also be any value in a range from 1 Hz up to 100 kHz. Thus, the processor 126 can vary the switching frequency according to the following examples of initial, final value pairs: (1 Hz, 1 kHz); (10 Hz, 1 kHz); (10 Hz, 20 kHz); (50 Hz, 1 kHz); (100 Hz, 25 kHz); (1 kHz, 5 kHz); (2 kHz, 40 kHz); (75 kHz, 20 kHz); (50 kHz, 25 kHz); (50 kHz, 1 Hz); (40 kHz, 40 Hz); (20 kHz, 2 Hz), (5 kHz, 50 Hz); and (5 kHz, 5 Hz). It should be understood that these pairs of initial and final switching frequency values are illustrative only and that various other combinations are within the scope of the claimed invention. As the example pairs illustrate, the spacing between the initial and final switching frequency values can vary. The spacing can be only a few Hertz, tens of Hertz, or a few kHz. Also, the initial switching frequency can be smaller or greater than the final switching frequency.

The variation of the switching frequency from the initial value to the final value is referred to as frequency sweep. The sweep typically occurs over a specified duration that can range from a few seconds up to a few minutes. In general, a specified duration is divided into a number of intervals. The intervals can be uniform or non-uniform, i.e., successive intervals can monotonically become larger or smaller. The intervals may also have randomly selected durations. The switch 124 is switched at the initial frequency during the first interval. In each of the successive intervals, the switching frequency is increased or decreased according to a step, and the switch 124 is switch at the final frequency during the last interval.

The mode in which the switching frequency is changed or swept can also be controlled by the processor 126. For example, the mode can be linear, i.e., the step is substantially constant and the switching frequencies in the successive intervals increase or decrease uniformly. As used herein, substantially constant means that the variation in successive steps is not more than 5 Hz. In one illustrative example of linear variation, the initial and final frequencies are 1 kHz and 20 kHz, respectively, a duration of 10 minutes is divided into 10 one-minute intervals and, accordingly, the step is 2 kHz.

The mode can also be non-linear, i.e., the steps in successive intervals can monotonically increase or decrease. In one illustrative example of non-linear variation, the initial and final frequencies are 50 kHz and 125 Hz, respectively, a duration of 10 minutes is divided into 10 one-minute intervals. The steps in the successive intervals are selected as 25 kHz, 12 kHz, 6 kHz, 3 kHz, 2 kHz, 1 kHz, 500 Hz, 250 Hz, and 125 Hz, respectively. In some embodiments, the mode can be a saw-tooth pattern, i.e., the switching frequency can increase, e.g., up to the final frequency or a fraction thereof, during each one of a first group of intervals. The switching frequency can then decrease, e.g., down to the initial frequency or down to another value greater than the initial frequency, during each one of a second group of intervals. This pattern can be repeated, i.e., the frequency can continue to increase during some intervals and then decrease in some other intervals. The switching frequencies in the various intervals may be selected such that in the last interval the switching frequency is set to the specified final value. When the saw-tooth mode is used, the initial and final frequency values can be the same.

Figure 2:
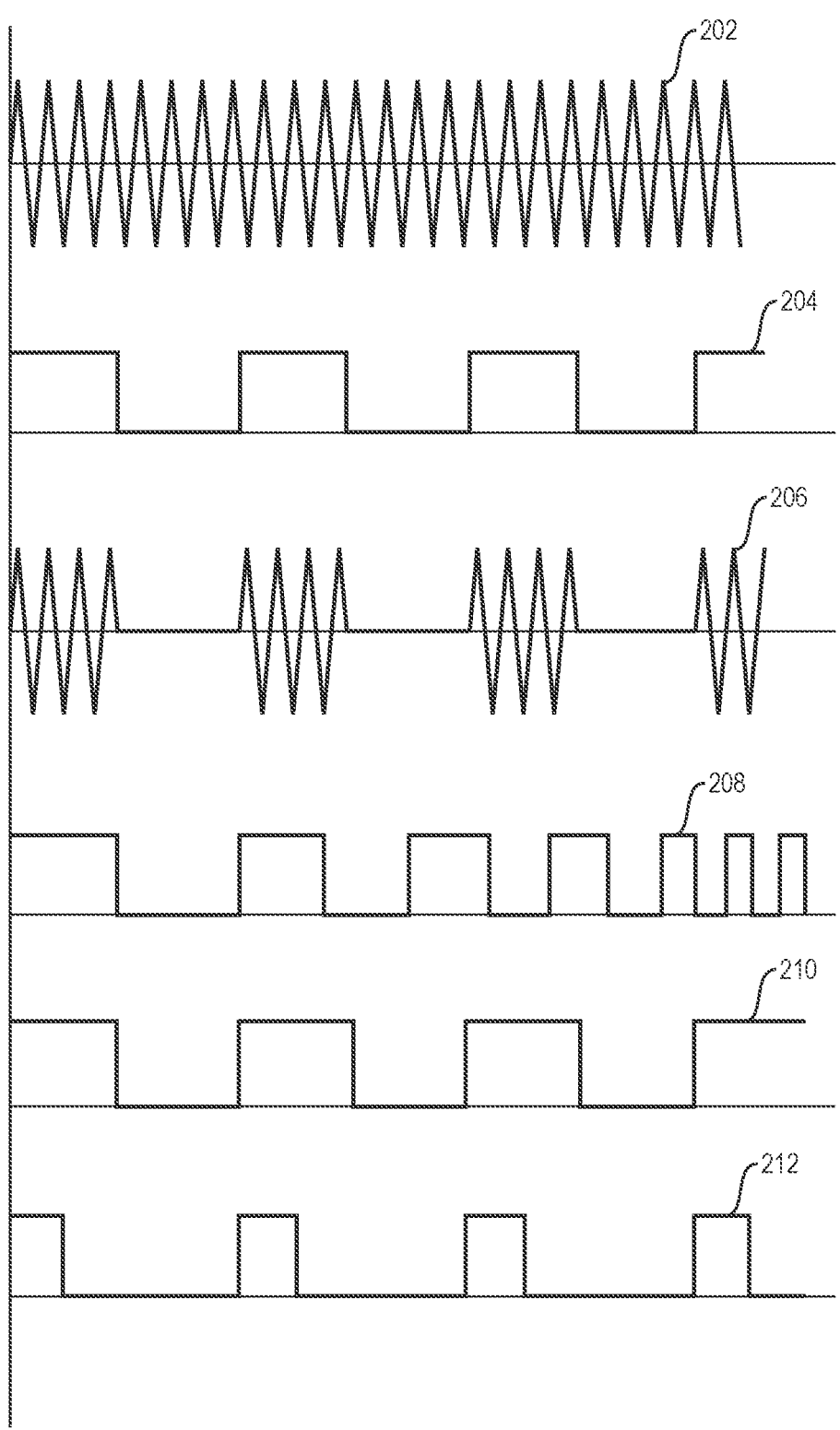
FIG. 2 illustrates various waveforms generated and/or used by a high voltage, variable frequency electromagnetic radiation system according to one embodiment.

With reference to FIG. 2, waveform 202 illustrates an unmodulated, substantially constant frequency carrier signal that can be observed at the port 114 if the switch 124 remains closed. The waveform 204 illustrates ON/OFF switching of the switch 124 and waveform 206 depicts a corresponding ON/OFF keying of the carrier signal depicted in the waveform 202. Waveform 208 depicts four successive intervals, as an example, in which the switching frequency varies from a low value to a high value. In the waveforms 210, 212, the switching frequency is the same but the duty cycle in the waveform 210 is approximately 50% and the duty cycle in the waveform 212 is approximately 25%

Referring back to FIG. 1, as the audio modulated, gain adjusted, variably ON/OFF keyed, and/or duty cycle adjusted carrier signal is supplied to the primary coil 118 of the resonant transformer, a relatively high voltage signal, e.g., a signal having an RMS voltage up to tens of kilovolts, is induced in the secondary coil 132 of the resonant transformer 118. The frequency of the induced signal varies from low order harmonics of the resonant frequency (e.g., 25 kHz, 50 kHz, 100 kHz, etc.) up to higher order harmonics thereof (e.g., 400 kHz, 600 kHz, etc.). Each of the tubes 134a-134d is filled with a different gas selected from inert and noble gases. The high, varying frequency voltage induced in the radiating terminal 136 of the secondary coil 132 can excite the tubes 134a-134d. Each tube, depending on the properties of the gas therein, may ignite at a different voltage-frequency combination and, in response, may emit a spectral emission of a particular wavelength. A person exposed to electromagnetic radiation received directly from the terminal 136 and/or to the spectral emissions from the tubes 134a-134d may experience therapeutic benefits, such as reduction of pain, anxiety, fatigue, etc.

To facilitate such therapeutic benefits, in some embodiments, the various parameters of the carrier frequency described above can be conveniently controlled by selecting a recipe. In one example, a recipe can include a mode (e.g., linear, non-liner, or saw-tooth), an initial frequency, an end frequency, and a duration (e.g., 30 seconds, 2 minutes, 15 minutes, 20 minutes, 30 minutes, etc.). As described above, both of the initial and final frequencies can be selected from the range of 1 Hz up to 100 kHz. Some recipes include one or more additional parameters such as an output scale factor that can control gain of the RMS voltage of the carrier, number of intervals into which the duration of the recipe is divided, interval spacing, i.e., whether the intervals are uniform or non-uniform, frequency steps, etc.

A memory coupled to the processor 126 can store one or more recipes in a recipe database, and the processor may execute a control app (a software system, in general) to control the system 100 according to the parameters specified in a recipe. A user interface can be used to display a list of available recipes to a user, who can then select a particular recipe. The user interface that may include a software component as part of the control app, and a display and/or a keyboard, and can be an integral part of the system 100. Alternatively or in addition, the user interface can be provided on another user device 138 that can communicate with the processor 126. A user app (another software system, in general) that can execute on the user device 138 may be used to communicate with the processor 126. The communication can be wired or wireless. Examples of the user device 138 include a smart phone, a tablet, a laptop or desktop computer, etc. In some embodiments, the recipe database may be stored on the user device 138 in addition to or instead of storing the recipe database on the system 100. A user may use the user app and a user interface associated therewith to select a recipe and the selected recipe may then be transmitted to the system 100 so that the processor 126 can control the operation of the system 100. If a recipe includes only the mode, start and end frequencies, and the duration, the processor may use a preset or default number of intervals (e.g., 5, 10, 12, 20 intervals), and may compute the switching frequency to be used to turn the switch 124 ON and OFF in each interval according to the specified mode.

In some embodiments, instead of using a recipe from a database, the user interface of the control and/or user app can be used to create a new recipe by including therein one or more system parameters described above. The user may also specify the default values of one or more parameters included in the recipe, and may store the new recipe in the recipe database. In other embodiments, via the control and/or user app a user may directly specify one or more system parameters individually, and not as part of any recipe. For example, a user may specify an output scale factor to adjust gain of the carrier, type of modulation (i.e., using stored audio, external audio, streamed audio, a combination thereof, or frequency sweep), and a duration. Using the user interface, one or more system parameters can be changed while the system 100 is in operation. For example, the duration can be increased, the gain can be adjusted, and/or the mode of frequency sweep can be changed.

In some embodiments, the control and/or user apps may access one or more current system parameters, e.g., the current gain, the RMS voltage of the carrier, switching frequency, mode, etc., and may display the values of those parameters using the corresponding user interface. The control and/or user apps may also permit a user to input a user-related characteristic such as day/time of use, the user's weight, pulse rate, blood pressure, mood, perceived effectiveness of a recipe, etc. A user profile can be generated by combining one or more user related characteristics, and one more user profiles can be stored on the user device 138 and/or the system 100 in a profile database.

In some embodiments, the control app and/or the user app can communicate with a server 140 via a network such as the Internet. Access to the network by the system 100, the user device 138, and/or the server 140 can be wired or wireless. The server may update or replace the control app installed on the system 100 and/or a user app installed on a user device 138. The server 140 may also update the recipe database, e.g., by adding one or more new recipes or by removing one or more stored recipes, or may replace a stored recipe database with a new recipe database. Different types of control and/or user apps provided by the server 140 can provide different functionality. For example, some control and/or user apps may permit a user to select stored recipes only. Some apps may additionally permit a user to create and store new recipes. Some apps may further allow the user to record one or more user-related characteristic, as described above, rank one or more recipes, e.g., in terms of effectiveness thereof as perceived by the user, and/or to upload one or more recipes, with or without the associated rankings, to the server 140.

In one embodiment, the server 140 is in electronic communication with a number of high voltage, multi-frequency radiation generation systems 100 and/or the respective user devices 138 used to interface with such systems. By interfacing with the respective control and/or user apps of the systems 100, the server 140 can receive data including recipes used and frequency of usage of one or more recipes in a day, week, month, season, etc. The server 140 may also collect from the systems 100 user-designated rankings and/or one or more user-related characteristics input by the users, as described above. In some embodiments, with user consent, the server 140 may collect data automatically at regular intervals, such as daily, weekly, etc. In other embodiments, the sever 140 collects only that data that is uploaded by the users, e.g., using the user apps.

Using these data, the server 140 can generate several correlations. For example, the server 140 can correlate the frequency of usage of recipes with a particular user characteristic such as blood pressure in a certain range, e.g., mild hypertension. Based on this correlation, the most frequently used or a top few most frequently used recipes by users of that particular condition can be identified. As another example, user pulse rate can be correlated with the type of mode used for frequency sweep. It should be understood that these correlations are illustrative only and, in general, the sever 140 can correlate any system parameter and/or recipe with any user-related characteristic.

Based on these correlations, the server 140 can recommend recipes and/or system parameters to a user having a certain characteristic. For example, the server can recommend a recipe to a user who may have joint pain, or a logarithmic sweep mode to a user experiencing anxiety, or sweep frequencies in a range from 25-30 kHz to user having chronic fatigue, or audio modulation according to a music of a particular genre to a user having a Lyme's disease. These examples are illustrative only, and the server can make various other recommendations for various user characteristics and/or conditions. A user can request a recommendation from the user app by entering one or more characteristics.

The server 140 can also provide a forum to permit registered users to exchange experiences relating to their use of the high voltage multi-frequency systems 100. In this forum, the users themselves can exchange recipes they created. Users may also search for recipes and/or system parameters used by other users who have a particular characteristic of interest, and may receive information about the perceived effectiveness of these recipes and parameters. Users may also combine two or more recipes obtained from the form to create a new recipe.

In some embodiments, the sensor 122 monitors the voltage and/or current in the secondary coil, in addition to sensing current passing through the primary coil 118. In one embodiment, the system 100 includes another sensor 142 that can monitor a user characteristic. Information about the observed characteristic is communicated to the processor 126, directly via the control app or via the user app. Based on the observed characteristic, and a recommendation received from the server 140, the processor 126 may dynamically adjust one or more system parameters. For example, even if a recipe currently in use specifies output scale/gain of 80%, based on monitored characteristics of the user, the processor may adjust the gain to 60%. The sensor 142 may also shut off the system 100 if certain conditions, e.g., heart rate below a specified threshold or above a different specified threshold, are observed. In some embodiments, the controller 126 may communicate with other systems/devices via a port 144 (e.g., an Ethernet port). For example, via the port 144 the controller may communicate with the electromagnetic radiation generation system, a remote controller 138 such as a smart phone, tablet, PC, etc., and/or with other user devices/controllers via a network such as the Internet.

Embodiments of control and/or user apps may be implemented using a conventional general purpose or a specialized digital computer or microprocessor(s) programmed according to the teachings of the present disclosure, as will be apparent to those skilled in the computer art. Appropriate software coding can readily be prepared by skilled programmers based on the teachings of the present disclosure, as will be apparent to those skilled in the software art. The invention may also be implemented by the preparation of integrated circuits or by interconnecting an appropriate network of conventional component circuits, as will be readily apparent to those skilled in the art.

One embodiment includes a computer program product which is a machine readable medium (media) having instructions stored thereon/in which can be used to program one or more hosts to perform any of the features presented herein. The machine readable medium can include, but is not limited to, one or more types of disks including floppy disks, optical discs, DVD, CD-ROMs, micro drive, and magneto-optical disks, ROMs, RAMs, EPROMs, EEPROMs, DRAMs, VRAMs, flash memory devices, magnetic or optical cards, nanosystems (including molecular memory ICs), or any type of media or device suitable for storing instructions and/or data. Stored on any one of the computer readable medium (media), the present invention includes software for controlling both the hardware of the general purpose/specialized computer or microprocessor, and for enabling the computer or microprocessor to interact with a human viewer or other mechanism utilizing the results of the present invention. Such software may include, but is not limited to, device drivers, operating systems, execution environments/containers, and applications.

The foregoing description of various embodiments of the claimed subject matter has been provided for the purposes of illustration and description. It is not intended to be exhaustive or to limit the claimed subject matter to the precise forms disclosed. Many modifications and variations will be apparent to the practitioner skilled in the art. Particularly, while the concept "component" is used in the embodiments of the systems and methods described above, it will be evident that such concept can be interchangeably used with equivalent concepts such as, class, method, type, interface, module, object model, and other suitable concepts. Embodiments were chosen and described in order to best describe the principles of the invention and its practical application, thereby enabling others skilled in the relevant art to understand the claimed subject matter, the various embodiments and with various modifications that are suited to the particular use contemplated.

While the invention has been particularly shown and described with reference to specific embodiments, it will be understood by those skilled in the art that various changes in form and detail may be made therein without departing from the spirit and scope of the invention as defined by the appended claims. The scope of the invention is thus indicated by the appended claims and all changes that come within the meaning and range of equivalency of the claims are therefore intended to be embraced.

What is claimed is:

1. A controller for controlling an electromagnetic radiation generation system comprising:
a processor; and
a memory coupled to the processor, the memory comprising a recipe database including a plurality of recipes and instructions, which if executed by the processor, program the processor to:
select, in response to a user input, at least one recipe from the recipe database; and
transmit the selected recipe to the electromagnetic radiation generation system, the recipe comprising:
a mode;
a start frequency and an end frequency; and
a duration.

2. The controller of claim 1, wherein the mode comprises at least one of: (i) a linear variation, (ii) an exponential variation, and (iii) a saw tooth variation.

3. The controller of claim 1, wherein the recipe further comprises at least one of an output scale factor and a pulse width factor.

4. The controller of claim 1, further comprising:
a voltage sensor sensing an output voltage of the electromagnetic radiation generation system; and
a current sensor sensing an output current of the electromagnetic radiation generation system,
wherein the controller is adapted to turn off the electromagnetic radiation generation system if at least one of: (i) the sensed output voltage exceeds a specified maximum voltage threshold, and (ii) the sensed output current exceeds a specified maximum current threshold.

5. The controller of claim 1, further comprising:
one of a smartphone, a tablet computer, a laptop, and a desktop computer, for wirelessly transmitting the recipe to the electromagnetic radiation generation system.

6. The controller of claim 1, wherein the instructions further program the processor to:
synthesize a new recipe in response to a user input corresponding to each parameter of the recipe; and
at least one of: (i) store the new recipe in the memory; and (ii) transmit the new recipe to a server.

* * * * *